United States Patent [19]

Portlock

[11] Patent Number: 4,460,775

[45] Date of Patent: Jul. 17, 1984

[54] 2-(3-MERCAPTO-1-OXOPROPYL)-1,2,3,4-TETRAHYDROISOQUINOLINE-1-CARBOXYLIC ACID DERIVATIVES

[75] Inventor: David E. Portlock, Norwich, N.Y.

[73] Assignee: Norwich Eaton Pharmaceuticals, Inc., Norwich, N.Y.

[21] Appl. No.: 65,195

[22] Filed: Aug. 9, 1979

[51] Int. Cl.$^3$ .................... C07D 217/16; A61K 31/47
[52] U.S. Cl. .................................. 546/147; 424/258
[58] Field of Search ........................................ 546/147

[56] References Cited

U.S. PATENT DOCUMENTS 4,256,751  3/1981  Hayashi et al. ...................... 546/147

FOREIGN PATENT DOCUMENTS 12845   7/1980  European Pat. Off. .
49605   4/1982  European Pat. Off. .
2470767 6/1981  France .

Primary Examiner—Donald G. Daus
Assistant Examiner—James H. Turnipseed
Attorney, Agent, or Firm—Anthony J. Franze

[57] ABSTRACT

Compounds of the formula:

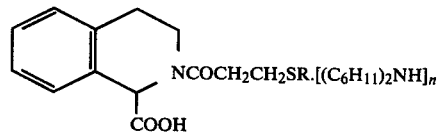

wherein R is H or

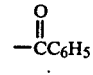

and n is 0 or 1 are useful as angiotensin I converting enzyme inhibitors.

6 Claims, No Drawings

2-(3-MERCAPTO-1-OXOPROPYL)-1,2,3,4-TETRAHYDROISOQUINOLINE-1-CARBOXYLIC ACID DERIVATIVES

This invention is concerned with chemical compounds and more particularly with compounds of the formula:

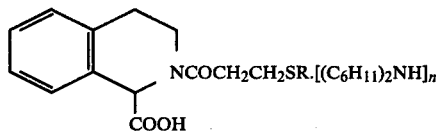

wherein R is H or

and n is 0 or 1. These compounds are useful as inhibitors of the enzyme responsible for the conversion of the decapeptide angiotensin I to the powerful pressor agent angiotensin II which has been implicated as the causative factor in various forms of hypertension in mammals. Their ability to intervene in and arrest the sequence whereby angiotensin II is produced by nullifying the enzyme causing the formation of that agent makes them useful in the treatment of hypertension.

The capacity of the compounds of this invention to inhibit angiotensin I converting enzyme is illustrated by the very small amounts of them necessary to secure at least 50% inhibition of the converting enzyme isolated from rabbit lung tissue, such amounts ranging from 1.98 to $10.0 \times 10^{-6}$ moles per liter.

The compounds of this invention can be readily prepared in a variety of forms such as tablets, capsules, elixirs, solutions and suspensions employing common excipients and adjuvants known to the art and with which there is no incompatability.

In order that this invention may be readily available to and understood by those skilled in the art, the following examples describe the now preferred methods for obtaining the compounds thereof.

EXAMPLE I

2-[(3-Benzoylthio)-1-oxopropyl]-1,2,3,4-tetrahydroisoquinoline-1-carboxylic Acid Dicyclohexylamine Salt To a solution of NaOH (4.8 g, 0.12 mole) in H$_2$O (120 ml) was added rapidly 1,2,3,4-tetrahydroisoquinoline-1-carboxylic acid hydrochloride (12.9 g, 0.060 mole), with cooling in an ice bath. Then a solution of NaOH (2.4 g, 0.060 mole) in H$_2$O (30 ml) and 3-bromopropionyl chloride (10.2 g, 0.060 mole) were added dropwise, simultaneously at 2°-4° over 30 minutes using rapid mechanical stirring. The mixture was further stirred in the cold for 10 minutes and at ambient temperature for 3.5 hours. Next a solution of potassium thiobenzoate (10.5 g, 0.060 mole) in H$_2$O (60 ml) was added rapidly (2 minutes) to the reaction mixture at 15° with rapid stirring, and then further stirred at ambient temperature overnight. The reaction solution was filtered, acidified with 20% HCL (13 ml) to pH of 2-3, extracted several times with ether (600 ml total), dried over Na$_2$SO$_4$, filtered, and concentrated under reduced pressure to dryness. The amorphous, free acid product was dissolved in acetonitrile (70 ml) and treated gradually with dicyclohexylamine (9.0 g, 0.050 mole) with cooling in an ice bath. Resultant cream-colored crystalline product was collected by filtration, washing with cold acetonitrile, ether; m.p. 167°-170°; yield: 20.0 g (60.3%). Recrystallization from absolute ethanol (125 ml) gave 14.4 g (43.5%) of product; m.p. 177°-184°.

Anal. Calcd. for C$_{20}$H$_{19}$NO$_4$S.(C$_6$H$_{11}$)$_2$NH: C, 69.48; H, 7.69; N, 5.09. Found: C, 69.76; H, 7.72; N, 5.06.

EXAMPLE II

2-[(3Mercapto)-1-oxopropyl]-1,2,3,4-tetrahydroisoquinoline-1-carboxylic Acid Dicyclohexylamine Salt A mixture of the compound of Example I and conc. ammonium hydroxide (240 ml) was heated on a steam bath to 80° in 16 minutes, using rapid mechanical stirring. The temperature was maintained at 80°-88° for 23 minutes, immediately cooled in ice bath to 25°, treated with Celite, filtered, and concentrated under water pump (bath at 50°-65°) to a volume of ca. 20 ml. The residue was treated with H$_2$O (10 ml) at ambient temperature with hand stirring, and the resultant small amount of white, crystalline solid was collected by filtration, washing with H$_2$O (15 ml). The filtrate (plus washings) was treated with ether (100 ml), cooled in an ice bath, and acidified with 20% HCl (6.5 ml) to pH of 1-2. The resultant mixture was filtered to remove a white, crystalline solid (1.1 g), and the aqueous phase was further extracted with ether (5x50 ml). The combined extracts were dried over Na$_2$SO$_4$, filtered, and evaporated to dryness under reduced pressure to give a viscous oil (9 g), which was diluted to 37 ml with acetone, cooled in an ice bath, and treated gradually with dicyclohexylamine (4.5 g, 0.025 mole). After storage in the refrigerator for 1 hour, the resultant white crystalline solid was collected and washed well with cold acetone, ether; m.p. 153°-155°; yield: 7.7 g (78%). Recrystallization of 5.6 g of the product from absolute ethanol (50 ml) gave m.p. 154°-156°; yield: 4.5 g (63%).

Anal. Calcd. for C$_{13}$H$_{15}$NO$_3$S.(C$_6$H$_{11}$)$_2$NH: C,67.23; H, 8.58; N, 6.27. Found: C, 67.14; H, 8.80; N, 6.30.

EXAMPLE III

2-[(3-Mercapto)-1-oxopropyl]-1,2,3,4-tetrahydroisoquinoline-1-carboxylic Acid

A mixture of the compound of Example II (9.3 g, 0.021 mole) and 2-propanol (100 ml) was acidified with a solution of dry HCl-2-propanol (10 ml), dropwise over 5 minutes, with cooling in an ice bath and hand stirring. The insoluble (C$_6$H$_{11}$)$_2$NH.HCl was collected, washing well with isopropanol, and the filtrate was concentrated to near dryness under reduced pressure (bath at 35°-45°). The residue was extracted with ether (100 ml total), dried over Na$_2$SO$_4$, filtered, and concentrated to near dryness under reduced pressure; the residue consisted of a viscous oil, 6.2 g. The oil was dissolved in CHCl$_3$ (75 ml), treated with Silica Gel (18.2 g), and stirred at 25°-30° for 1.5 hours. The mixture was filtered, washed well with CHCl$_3$, and the filtrate was concentrated to dryness under reduced pressure (bath at 30°-35°). The product residue consisted of an amorphous solid, 3.4 g (36%), which was dried in a KOH-pistol at room temperature for 5 days.

Anal. Calcd. for $C_{13}H_{15}NO_3SO.\frac{1}{4}H_2O$: C, 57.87; H, 5.79; N, 5.19; $H_2O$, 1.7%; Found: C, 57.90; H, 5.76; N, 5.23; $H_2O$, 4.4%.

What is claimed is:

1. A compound of the formula:

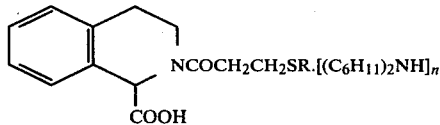

wherein R is H or

and n is 0 or 1.

2. The compound 2-[(3-benzoylthio)-1-oxopropyl]-1,2,3,4-tetrahydroisoquinoline-1-carboxylic acid dicyclohexylamine salt.

3. The compound 2-[(3-mercapto)-1-oxopropyl]-1,2,3,4-tetrahydroisoquinoline-1-carboxylic acid dicyclohexylamine salt.

4. The compound 2-[(3-mercapto)-1-oxopropyl]-1,2,3,4-tetrahydroisoquinoline-1-carboxylic acid.

5. A compound of the formula:

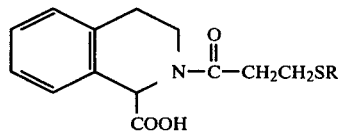

wherein R is H or

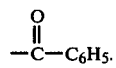

6. A compound of the formula:

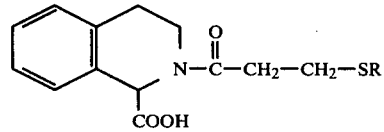

wherein R is H or

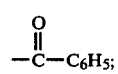

and the sodium and dicyclohexylamine salts thereof.

* * * * *